(12) United States Patent
Kitamura

(10) Patent No.: US 9,307,948 B2
(45) Date of Patent: Apr. 12, 2016

(54) IMAGE PROCESSING APPARATUS, METHOD, AND PROGRAM

(71) Applicant: FUJIFILM Corporation, Tokyo (JP)

(72) Inventor: Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/481,741

(22) Filed: Sep. 9, 2014

(65) Prior Publication Data

US 2014/0376796 A1     Dec. 25, 2014

Related U.S. Application Data

(63) Continuation of application No. PCT/JP2013/001528, filed on Mar. 8, 2013.

(30) Foreign Application Priority Data

Mar. 13, 2012    (JP) ................................ 2012-055599

(51) Int. Cl.
    *G06K 9/00*        (2006.01)
    *A61B 6/00*        (2006.01)
    *G06T 7/00*        (2006.01)
    *A61B 6/03*        (2006.01)

(52) U.S. Cl.
    CPC ................. *A61B 6/5217* (2013.01); *A61B 6/50* (2013.01); *A61B 6/504* (2013.01); *G06T 7/0012* (2013.01); *G06T 7/0085* (2013.01); *G06T 7/0093* (2013.01); *A61B 6/032* (2013.01); *A61B 6/505* (2013.01); *G06T 2207/10081* (2013.01); *G06T 2207/20016* (2013.01); *G06T 2207/20024* (2013.01); *G06T 2207/20144* (2013.01); *G06T 2207/30061* (2013.01)

(58) Field of Classification Search
    CPC ......................................................... G06T 7/00
    USPC ......................................................... 382/131
    See application file for complete search history.

(56) References Cited

U.S. PATENT DOCUMENTS

| 7,020,314 B1 | 3/2006 | Suri et al. |
| 2011/0064289 A1 | 3/2011 | Bi et al. |

(Continued)

FOREIGN PATENT DOCUMENTS

| EP | 2 372 646 A2 | 10/2011 |
| JP | 2011-104206 A | 6/2011 |
| JP | 2011-206531 A | 10/2011 |
| WO | WO 03/042712 A1 | 5/2003 |

OTHER PUBLICATIONS

International Search Report (ISR) (PCT Form PCT/ISA/210), in PCT/JP2013/001528, dated Jul. 2, 2013.

(Continued)

*Primary Examiner* — Stephen R Koziol
*Assistant Examiner* — Delomia L Gilliard
(74) *Attorney, Agent, or Firm* — McGinn IP Law Group, PLLC

(57) ABSTRACT

The filtering unit calculates an evaluation matrix by performing filtering on each pixel position of an image representing a hollow structure using a second order partial differential of a function representing a hollow sphere. The evaluation unit calculates an evaluation value of at least one or more of point-like structureness, line-like structureness, and plane-like structureness at the pixel position based on the calculated evaluation matrix.

13 Claims, 6 Drawing Sheets

(56) References Cited

U.S. PATENT DOCUMENTS

2011/0075920 A1    3/2011  Wu et al.
2011/0222748 A1*   9/2011  Kitamura .................. 382/128
2012/0089025 A1*   4/2012  Toji ........................... 600/443
2013/0108133 A1*   5/2013  Inoue ......................... 382/131

OTHER PUBLICATIONS

A.F. Frangi et al., "Multiscale vessel enhancement filtering", Proceedings of MICCAI, vol. 1496, pp. 130-137, 1998.

M.W.K. Law and A.C.S. Chung, "Three Dimensional Curvilinear Structure Detection Using Optimally Oriented Flux", Proceedings of ECCV, Part IV, LNCS 5305, pp. 368-382, 2008.

Y.Y. Boykov and M.P. Jolly, "Interactive Graph Cuts for Optimal Boundary & Region Segmentation of Objects in N-D Images", Proceedings of International Conference on Computer Vision, vol. 1, pp. 105-112, 2001.

A. Kanitsar et al., "CPR—Curved Planar Reformation", IEEE Visualization, 2002.

M. Oda et al., "Development of a lymph node detection method from 3D abdominal CT images using multi shape ellipsoidal structure detection filter", IEICE Technical Report, vol. 111, No. 389, pp. 251-256, 2012.

* cited by examiner

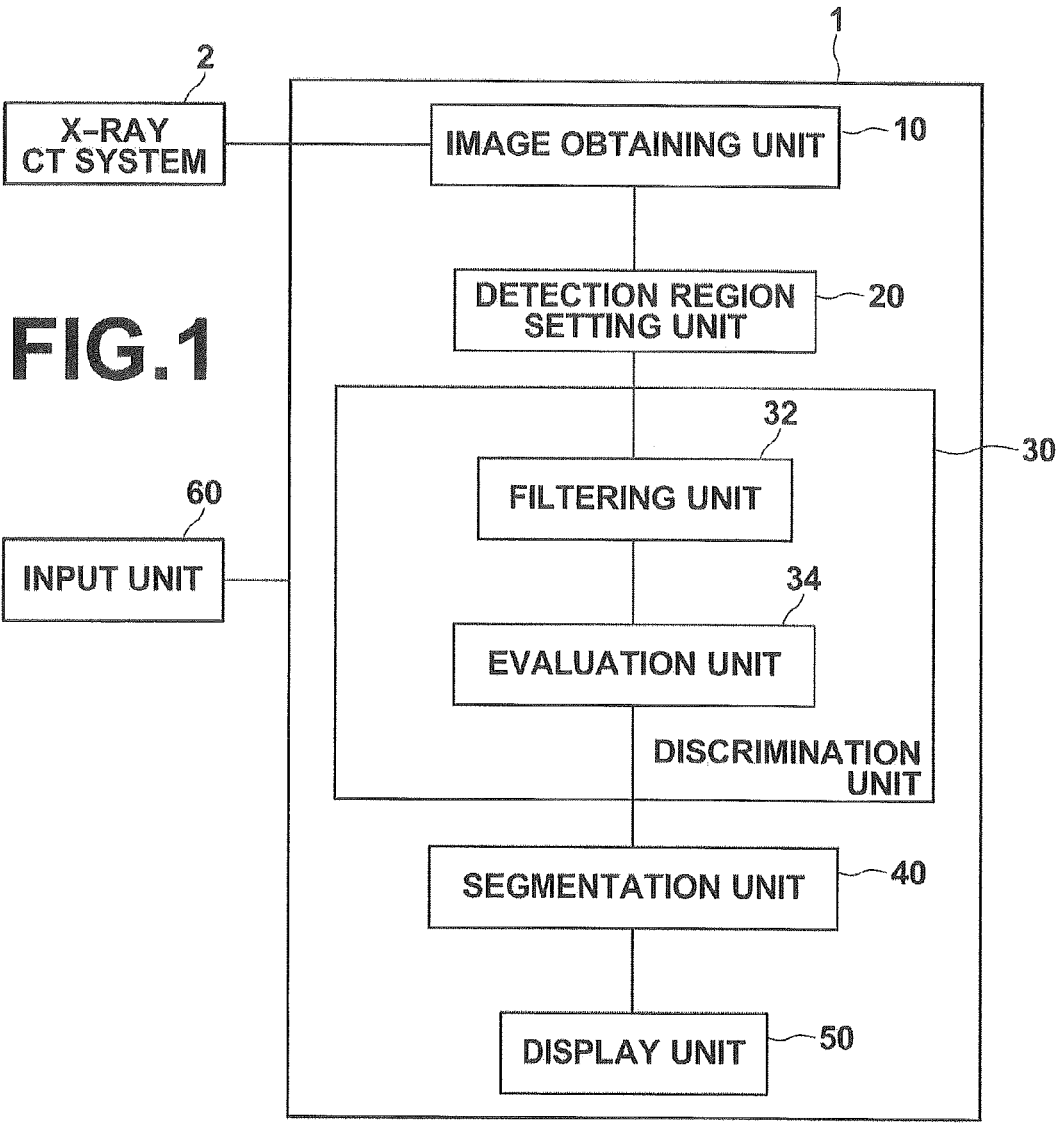
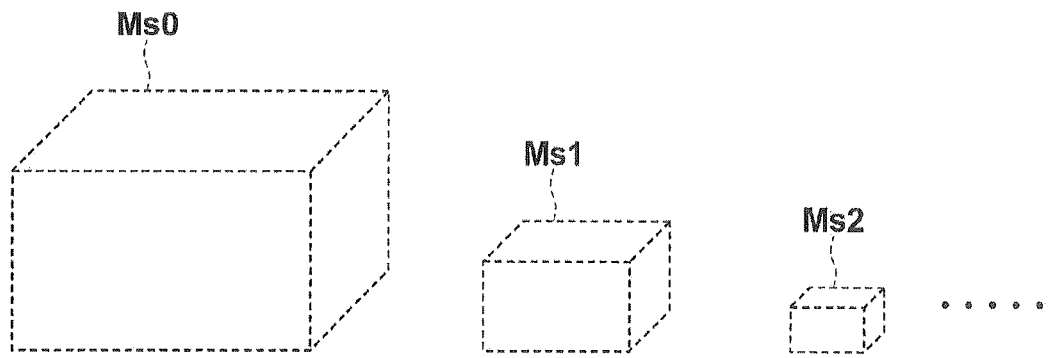

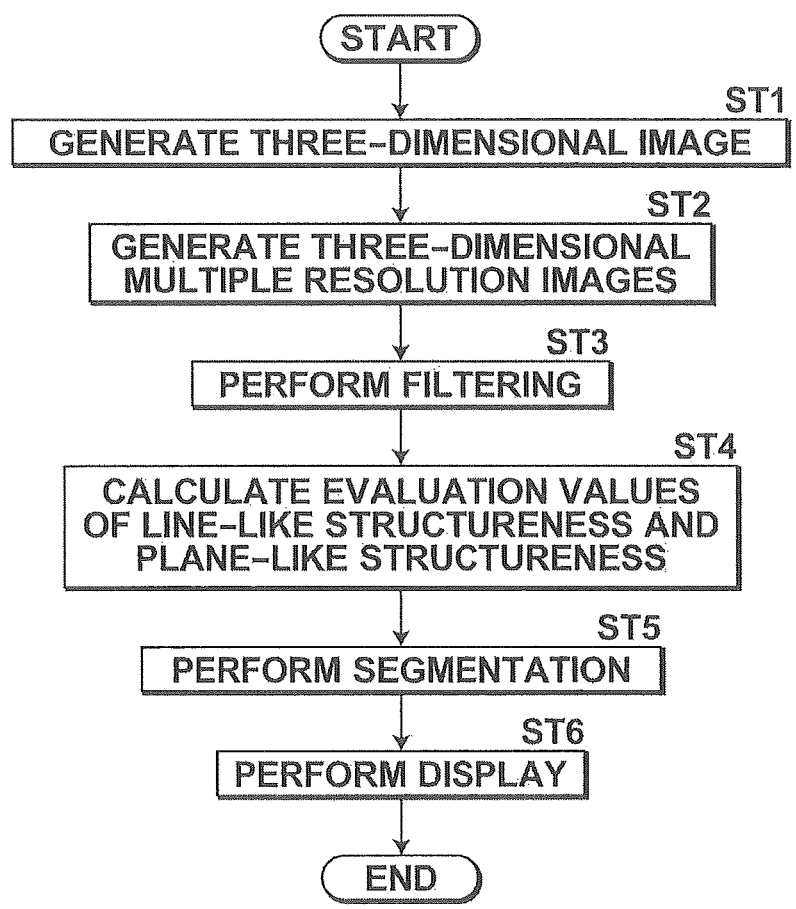

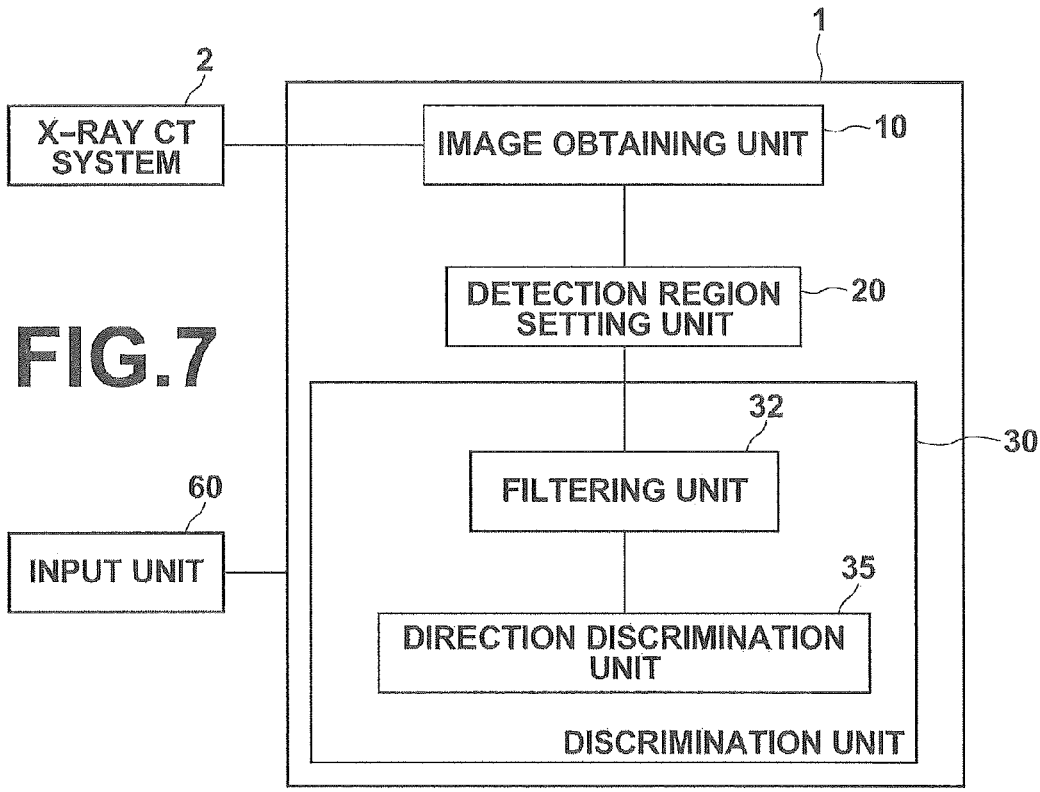
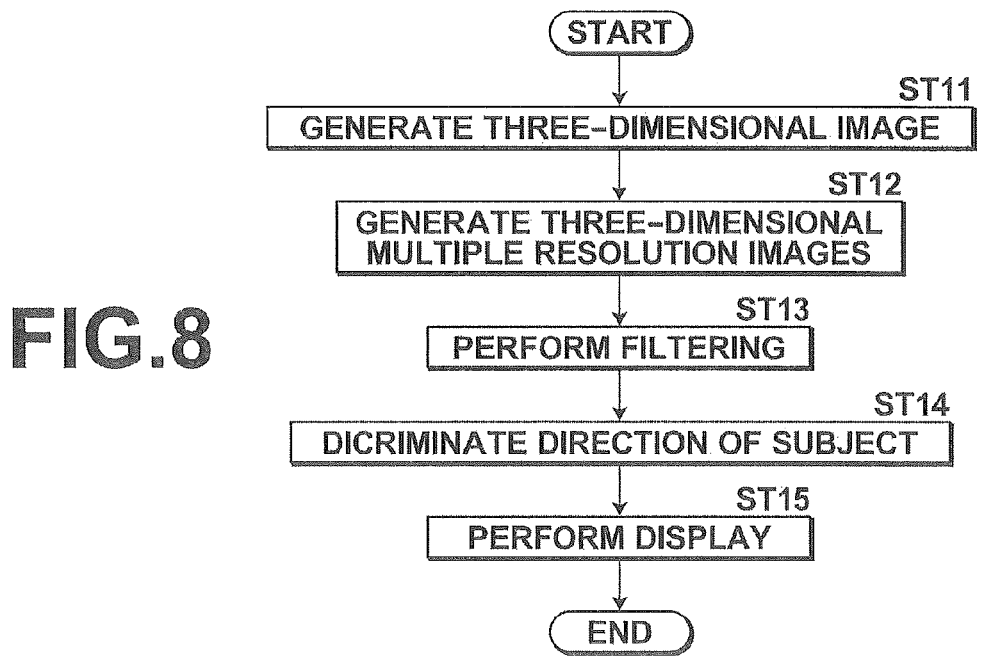

IMAGE PROCESSING APPARATUS, METHOD, AND PROGRAM

CROSS-REFERENCE TO RELATED APPLICATIONS

This application is a Continuation of PCT International Application No. PCT/JP2013/001528 filed on Mar. 8, 2013, which claims priority under 35 U.S.C. §119 (a) to Japanese Patent Application No 2012-055599 filed on Mar. 13, 2012. Each of the above applications is hereby expressly incorporated by reference, in its entirety, into the present application.

BACKGROUND OF THE INVENTION

1. Technical Field

The present invention relates to an image processing apparatus and method for discriminating a structure of a hollow structure in an image, and a program for causing a computer to perform the image processing method. It is a further object of the present invention to provide an image processing apparatus for discriminating a principal axis direction or a normal direction of a hollow structure in an image.

2. Background Art

Recently, high quality three-dimensional images have been used in image diagnosis with the advancement of medical equipment (e.g., multidetector CT and the like). As a three-dimensional image is formed of a multiple of two-dimensional images and has a large amount of information, the doctor may sometimes require a prolonged time to find out a desired observation region and give a diagnosis. Consequently, it is practiced to extract an organ of interest and perform MIP, VR, or CPR display, or the like, in order to enhance the visibility of an entire organ or a lesion and improve efficiency of diagnosis.

In the meantime, as a method of extracting a blood vessel or a bone in a medical image, Hessian analysis using a Hessian matrix is proposed (refer to A. F. Frangi et al., "Multiscale vessel enhancement filtering", Proceedings of MICCAI, Vol. 1496, pp. 130-137, 1998). The Hessian analysis discriminates whether a local structure in an image is a point, a line, or a plane by analyzing eigenvalues of a Hessian matrix whose elements are second order partial differential coefficients calculated by the use of the second differential kernel of a given filter, such as Gaussian kernel or the like. The use of the Hessian analysis allows a blood vessel and a bone to be discriminated as a line-like structure and a plate-like structure respectively.

There are cases, however, in which, if another structure is present in the vicinity of a line-like structure (vicinity structure), the method of A. F. Frangi et al., "Multiscale vessel enhancement filtering", Proceedings of MICCAI, Vol. 1496, pp. 130-137, 1998 erroneously discriminates the vicinity structure as the line-like structure. The method of M. W. K. Law and A. C. S. Chung, "Three Dimensional Curvilinear Structure Detection Using Optimally Oriented Flux", Proceedings of ECCV, Part IV, LNCS 5305, pp. 368-382, 2008 improves the filter proposed in A. F. Frangi et al., "Multiscale vessel enhancement filtering", Proceedings of MICCAI, Vol. 1496, pp. 130-137, 1998 by convoluting a function representing a solid sphere (solid sphere model function) with the inside of the spherical shape as 1 and the outside as 0 and limiting the calculation range of the second order partial differential coefficients to the surface of the sphere in Hessian analysis, whereby the influence of the vicinity structure on the filtering result may be reduced.

DISCLOSURE OF THE INVENTION

But, the solid sphere model represented by the solid sphere model function in the method of M. W. K. Law and A. C. S. Chung, "Three Dimensional Curvilinear Structure Detection Using Optimally Oriented Flux", Proceedings of ECCV, Part IV, LNCS 5305, pp. 368-382, 2008 has structural characteristics that the inside is filled with a certain filling material, so that the structural characteristics do not match those of a hollow structure having a hollow space inside, such as a bronchus structure in a medical image. Therefore, the application of the method that convolutes the solid sphere model function disclosed in M. W. K. Law and A. C. S. Chung, "Three Dimensional Curvilinear Structure Detection Using Optimally Oriented Flux", Proceedings of ECCV, Part IV, LNCS 5305, pp. 368-382, 2008 to an image that includes a hollow structure will result in that errors and the like are likely to occur in the results of the filtering due to the difference in structural characteristics between the shape represented by the model function and the hollow structure, and there is a limit to the accuracy of the results of the Hessian analysis.

Therefore, it is sought that more accurately discrimination of a local shape (at least one or more of point-like structureness, line-like structureness, and plane-like structureness) of a hollow structure be made by improving the accuracy of the filtering and based on the evaluation matrix obtained as the result of the filtering. Likewise, it is sought that the axial direction of a line-like structure or a normal direction of a plate-like structure be discriminated more accurately by improving the accuracy of the filtering and based on the evaluation matrix obtained as a result of the filtering.

The present invention has been developed in view of the circumstances described above, and it is an object of the present invention to improve discrimination accuracy of at least one or more of point-like structureness, line-like structureness, and plane-like structureness of a hollow structure included in an image. It is a second object of the present invention to well discriminate an axial direction of the line-like structure or a normal direction of the plate-like structure included in the image.

An image processing apparatus according to a first aspect of the present invention includes a filtering unit that calculates an evaluation matrix by performing filtering on each pixel position of an image representing a hollow structure using a second order partial differential of a function representing a hollow sphere, and an evaluation unit that calculates an evaluation value of at least one or more of point-like structureness, line-like structureness, and plane-like structureness at the pixel position based on the calculated evaluation matrix.

An image processing method according to the first aspect of the present invention includes the steps of calculating an evaluation matrix by performing filtering on each pixel position of an image representing a hollow structure using a second order partial differential of a function representing a hollow sphere, and calculating an evaluation value of at least one or more of point-like structureness, line-like structureness, and plane-like structureness at the pixel position based on the calculated evaluation matrix.

An image processing program according to the first aspect of the present invention causes a computer to function as a filtering unit that calculates an evaluation matrix by performing filtering on each pixel position of an image representing a hollow structure using a second order partial differential of a function representing a hollow sphere, and an evaluation unit that calculates an evaluation value of at least one or more of point-like structureness, line-like structureness, and plane-like structureness at the pixel position based on the calculated evaluation matrix.

An image processing apparatus according to a second aspect of the present invention includes a filtering unit that calculates an evaluation matrix by performing filtering on each pixel position of an image representing a hollow structure using a second order partial differential of a function representing a hollow sphere, and a direction discrimination unit that calculates eigenvalues and eigenvectors by performing eigenvalue analysis on the calculated evaluation matrix and discriminates, based on directions of the calculated eigenvectors, a principal axis direction of a line-like structure or a normal direction of a plane-like structure.

The "hollow structure" described above may be any structure as long as at least a portion of the interior thereof is hollow. For example, the hollow structure may be a tubular (line-like) structure, such as a bronchus or the like, a hollow particle-like (point-like) structure, or a hollow plane-like structure. Further, the hollow structure may be a two-dimensional structure or a three-dimensional structure.

Preferably, the function representing the hollow sphere is expressed by Formula (3) given below:

$$\left. \begin{array}{l} f(r) = \delta(r - R) \\ r = \sqrt{x^2 + y^2 + z^2} \end{array} \right\} \quad (3)$$

where, x, y, z are three-dimensional coordinates in real space and R is the radius of the hollow sphere.

In the image processing apparatuses according to the first and second aspects of the present invention, the filtering unit calculates, with respect to functions representing the hollow sphere in a plurality of sizes, an evaluation value by performing filtering using a second order partial differential of a function representing each hollow sphere.

In the image processing apparatuses according to the first or the second aspect of the present invention, the filtering unit preferably performs the filtering using the second order partial differential of the function representing the hollow sphere in Fourier space.

Further, in the image processing apparatuses according to the first or the second aspect of the present invention, the image is preferably a medical image, and the hollow structure is preferably a bronchus.

According to the first aspect of the present invention, a filtering unit that calculates an evaluation matrix by performing filtering on each pixel position of an image representing a hollow structure using a second order partial differential of a function representing a hollow sphere, and an evaluation unit that calculates an evaluation value of at least one or more of point-like structureness, line-like structureness, and plane-like structureness at the pixel position based on the calculated evaluation matrix. This allows image filtering by a function representing a hollow sphere appropriately representing structural characteristics of a discrimination target to be performed. Consequently, the evaluation accuracy of an evaluated structure or structures of point-like structure, line-like structure, and plane like structure of a hollow structure included in an image may be improved based on evaluation values calculated from an evaluation matrix obtained as a result of the appropriate filtering.

According to the second aspect of the present invention, a filtering unit that calculates an evaluation matrix by performing filtering on each pixel position of an image representing a hollow structure using a second order partial differential of a function representing a hollow sphere, and a direction discrimination unit that calculates eigenvalues and eigenvectors by performing eigenvalue analysis on the calculated evaluation matrix and discriminates, based on directions of the calculated eigenvectors, a principal axis direction of a line-like structure or a normal direction of a plane-like structure. This allows image filtering by a function representing a hollow sphere appropriately representing structural characteristics of a discrimination target to be performed. Consequently, the accuracy of eigenvalues and eigenvector values calculated from the evaluation matrix may be improved. Therefore, an axis direction of a line-like structure or a normal direction of a plane-like structure may be discriminated appropriately on each position of a hollow structure based on the eigenvalue and eigenvector.

BRIEF DESCRIPTION OF DRAWINGS

FIG. 1 is a schematic block diagram of an image processing apparatus according to a first embodiment of the present invention, illustrating a configuration thereof.

FIG. 2 is a drawing for explaining a multiple resolution transformation.

FIG. 6 is a flowchart of processing performed in the first embodiment of the present invention.

FIG. 7 is a schematic block diagram of an image processing apparatus according to a second embodiment of the present invention, illustrating a configuration thereof.

FIG. 8 is a flowchart of processing performed in the second embodiment of the present invention.

BEST MODE FOR CARRYING OUT THE INVENTION

Figure 3A:
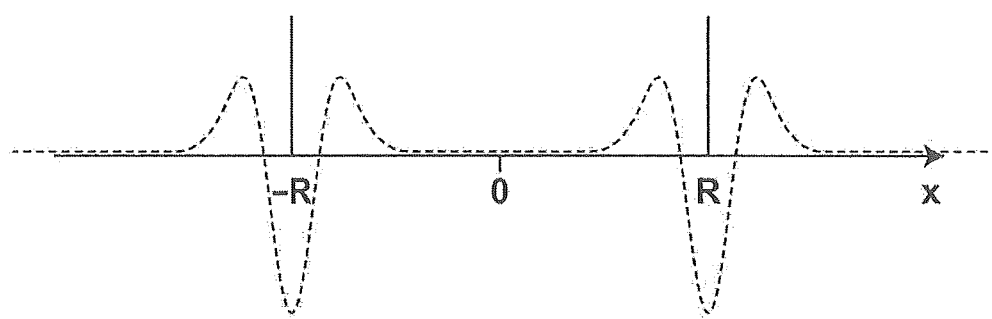
FIG. 3A is a drawing for explaining a solid sphere model function (part 1).

Hereinafter, embodiments of the present invention will be described with reference to the accompanying drawings. FIG. 1 is a schematic block diagram of an image processing apparatus according to an embodiment of the present invention, illustrating a configuration thereof. The configuration of the image processing apparatus 1 shown in FIG. 1 is realized by executing a program read into an auxiliary storage (not shown) on a computer (e.g., personal computer). The program is provided being recorded on an information storage medium, such as CD-ROM and the like, or distributed via a network, such as the Internet, and installed on a computer.

The image processing apparatus 1 generates a three-dimensional image M0 using a plurality of two-dimensional images captured, for example, by an X-ray CT system 2 and automatically segments a line-like structure and a plate-like structure included in the three-dimensional image M0. The image processing apparatus 1 includes an image obtaining unit 10, a detection region setting unit 20, a discrimination unit 30, a segmentation unit 40, a display unit 50, and an input unit 60.

The image obtaining unit 10 obtains a plurality of CT images (two-dimensional images) captured, for example, by the X-ray CT system 2, and generates a three-dimensional image M0 from the plurality of two-dimensional images. The image obtaining unit 10 may be a unit that obtains two-dimensional images, such as so-called MRI images, RI images, PET images, X-ray images, and the like, as well as CT images.

The detection region setting unit 20 first makes the voxel dimensions of the three-dimensional image M0 isotropic. For example, if the voxel dimensions of the three-dimensional image M0 are 0.3 mm, 0.3 mm, and 0.6 mm with respect to X, Y, and Z directions of the three-dimensional image M0 respectively, they are made isotropic to (X, Y, Z)=(0.5, 0.5, 0.5) (mm). By making the voxel dimensions of the three-dimensional image M0, kernel of the same size may be applied to each of the X, Y, and Z directions in the discrimination unit 30, to be described later, and the calculation may be simplified.

The detection region setting unit 20 performs a multiple resolution transformation on the three-dimensional image M0 after making the image isotropic and generates a plurality of three-dimensional multiple resolution images Msi (i=0 to n) (Gaussian pyramid) as shown in FIG. 2. Note that i=0 represents the same resolution as the resolution of the three-dimensional image M0 and i=n represents the lowest resolution. The voxel dimensions of the three-dimensional multiple resolution images Msi are (X, Y, Z)=(0.5, 0.5, 0.5), (1.0, 1.0, 1.0), (2.0, 2.0, 2.0), and so on in descending order of resolution.

The discrimination unit 30 includes a filtering unit 32 and an evaluation unit 34. The filtering unit 32 performs filtering on each of the three-dimensional multiple resolution images Msi using a hollow sphere model function and a Gaussian kernel in order to perform Hessian analysis using a Hessian matrix (evaluation matrix). That is, a filter kernel of the same size is convoluted with each of the multiple resolution images Msi having different resolutions. For the radius R of the hollow sphere represented by the hollow sphere model function and the Gaussian kernel size ($\sigma$), appropriate values are set based on the knowledge acquired by preliminary analysis and the like. For the radius R of the hollow sphere, a value which is at least greater than the Gaussian kernel size is set.

By convoluting the filter kernel of the same size (e.g., R=2.0 (voxels), $\sigma$=0.5 (voxels)) with each of the three-dimensional multiple resolution images Msi, filter kernels of different sizes are applied, in effect, to the three-dimensional image M0, so that a point-like structure, a line-like structure (e.g., bronchus), and a plate-like structure (e.g., bone, such as cortical bone) having different sizes may be detected. In other words, with respect to functions representing the hollow sphere with radius R in a plurality of sizes, an evaluation matrix is calculated by performing filtering using second order partial differential matrix of a function representing each hollow sphere.

The Hessian analysis of the present embodiment will now be described. The Hessian matrix used for the Hessian analysis is a 3×3 matrix for the three-dimensional image, as indicated in Formula (1) given below.

$$\nabla^2 I = \begin{bmatrix} Ixx & Ixy & Ixz \\ Iyx & Iyy & Iyz \\ Izx & Izy & Izz \end{bmatrix} \quad (1)$$

$$Ixx = \frac{\partial^2 I}{\partial x^2},$$

$$Ixy = \frac{\partial^2 I}{\partial x \partial y},$$

Each of the elements of the Hessian matrix Ixx, Ixy, Iyy, Iyz, Izz, Izx is calculated by performing filtering (convolution operation) on the image data of a target image using second order partial differentials of a hollow sphere model function f(r) and a Gaussian kernel function g(r).

In the present embodiment, the filtering processing is performed in Fourier space. First, the image data of a target image are Fourier transformed. Then, the Fourier transformed target image (FT (image)) is multiplied by the solid sphere model function, the Gaussian kernel function, and the second order partial differential, each being Fourier transformed. Then, by performing a reverse Fourier transform on the multiplication result, the filtering result is obtained. Note that the obtained filtering result is the same as the filtering result obtained by performing a convolution operation in real space. If the Fourier transform of the hollow sphere model function is taken as F($\upsilon$) and the Fourier transform of the Gaussian kernel function is taken as G($\upsilon$), the above relationship may be represented by Formula (2) given below.

$$FT^{-1}(FT(\text{image}) \times F(v) \times G(v) \times (2\pi v_x)^l \times (2\pi v_y)^m \times (2\pi v_z)^n) \quad (2)$$

Here, the hollow sphere model function f(r) may be defined by a delta function $\delta(r-R)$ as indicated in Formula (3) given below. Note that Formula (4) obtained by Fourier transforming Formula (3) is used in Formula (2) in order to perform the filtering in the Fourier space.

$$\left. \begin{array}{l} f(r) = \delta(r - R) \\ r = \sqrt{x^2 + y^2 + z^2} \end{array} \right\} \quad (3)$$

$$\left. \begin{array}{l} F(v) = \dfrac{\sin(Rv)}{Rv} \\ v = \sqrt{v_x^2 + v_y^2 + v_z^2} \end{array} \right\} \quad (4)$$

where, x, y, z in Formula (3) are the three-dimensional axes in real space, and R is the radius of the hollow sphere. The polar coordinate representation of the variable (frequency) of the three-dimensional Fourier space is expressed as $\upsilon=(\upsilon_x^2+\upsilon_y^2\upsilon_z^2)^{1/2}$.

The Fourier transformed Gaussian kernel function G($\upsilon$) in Formula (2) is expressed by the following formula.

$$G(v) = \exp\left(-\frac{v^2 \sigma^2}{2}\right) \quad (5)$$

The Gaussian kernel function G($\upsilon$) is used to give flexibility to the differential range of pixel values of the target image as in A. F. Frangi et al., "Multiscale vessel enhancement filtering", Proceedings of MICCAI, Vol. 1496, pp. 130-137, 1998 and M. W. K. Law, and A. C. S. Chung, "Three Dimensional Curvilinear Structure Detection Using Optimally Oriented Flux", Proceedings of ECCV, Part IV, LNCS 5305, pp. 368-382, 2008.

In Formula (2), the part $(2\pi\upsilon_x)^l \times (2\pi\upsilon_y)^m \times (2\pi\upsilon_z)^n$ corresponds to the differential processing in the Fourier space and a value corresponding to each of the elements Ixx, Ixy, Iyy, Iyz, Izz, and Izx may be calculated by assigning coefficients l, m, n corresponding to the respective differential directions in Formula (2) such that l+m+n=2 (0≤l, 0≤m, 0≤n). For example, the element Ixx which is second order partial differential value in x direction in the Hessian matrix at a processing target pixel of the three-dimensional multiple resolution images Msi may be calculated by assigning l=2 in x direction and m=n=0 with respect to Y and Z directions in Formula (2). Further, the element Ixy in the Hessian matrix at a processing target pixel of the three-dimensional multiple resolution images Msi may be calculated by assigning l=m=1 with respect to X and Y directions and n=0 with respect to Z direction in Formula (2).

Figure 4:
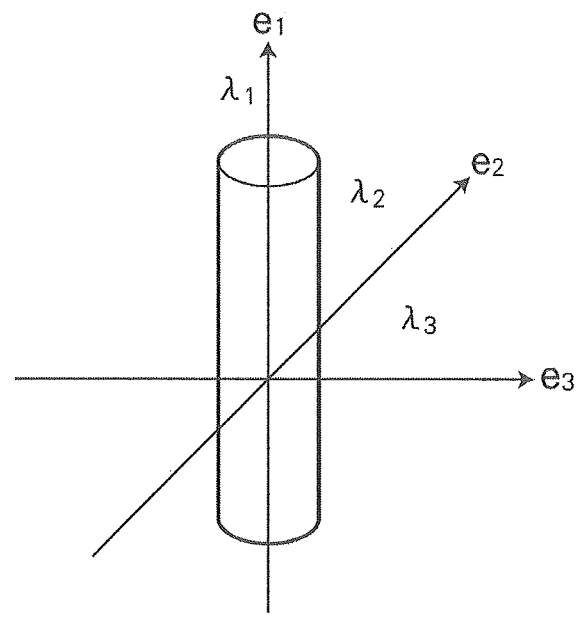
FIG. 4 is a drawing for explaining eigenvalues of a line-like structure.

When eigenvalues are obtained by applying eigenvalue decomposition to the Hessian matrix calculated in the manner described above, it is known that a line-like structure has characteristics that two of the three eigenvalues are relatively large while the remaining one is close to 0, as shown in FIG. 4. For example, eigenvalues of Formula (1) have the relationship of Formula (6) with a target tissue of a line-like structure. It is assumed that the eigenvalues are $|\lambda_1|<|\lambda_2|\lambda_3|$.

Eigenvalues of $\nabla^2 I$: $\lambda 1, \lambda 2, \lambda 3$ $$\left.\begin{array}{l} \lambda 1 \approx 0 \\ \lambda 2 \gg 0 \\ \lambda 3 \gg 0 \end{array}\right\} \quad (6)$$

Figure 5:
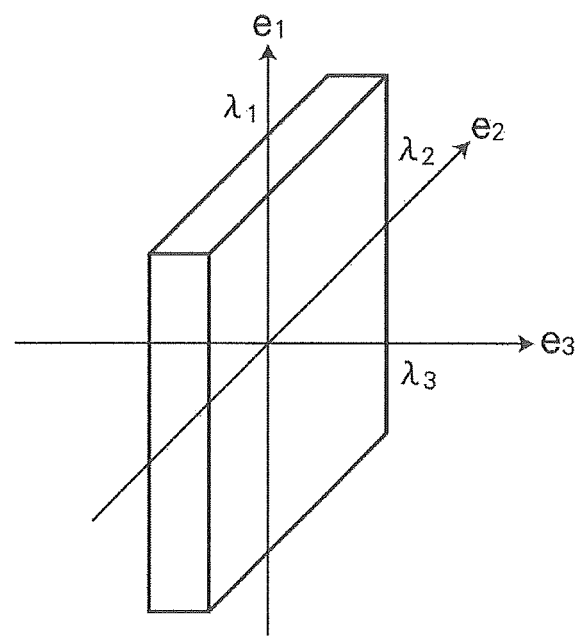
FIG. 5 is a drawing for explaining eigenvalues of a plate-like structure.

Further, it is known that a plate-like structure has characteristics that one of the three eigenvalues is large while the remaining two are close to 0, as shown in FIG. 5. For example, eigenvalues of Formula (1) have the relationship of Formula (7) with a target tissue of a plate-like structure.

$$\left.\begin{array}{l} \lambda 1 \approx 0 \\ \lambda 2 \approx 0 \\ \lambda 3 \gg 0 \end{array}\right\} \quad (7)$$

Still further, it is known that a point-like structure has characteristics that all three eigenvalues are large. For example, eigenvalues of Formula (1) have the relationship of Formula (8) with a target tissue of a point-like structure.

$$\left.\begin{array}{l} \lambda 1 \gg 0 \\ \lambda 2 \gg 0 \\ \lambda 3 \gg 0 \end{array}\right\} \quad (8)$$

Therefore, line-like structureness, plane-like structureness, and point-like structureness may be discriminated from the eigenvalues, and a bronchus region which is a line-like structure and a bone region which is a plate-like structure may be segmented in the three-dimensional image M0 using the discrimination results.

Figure 3B:
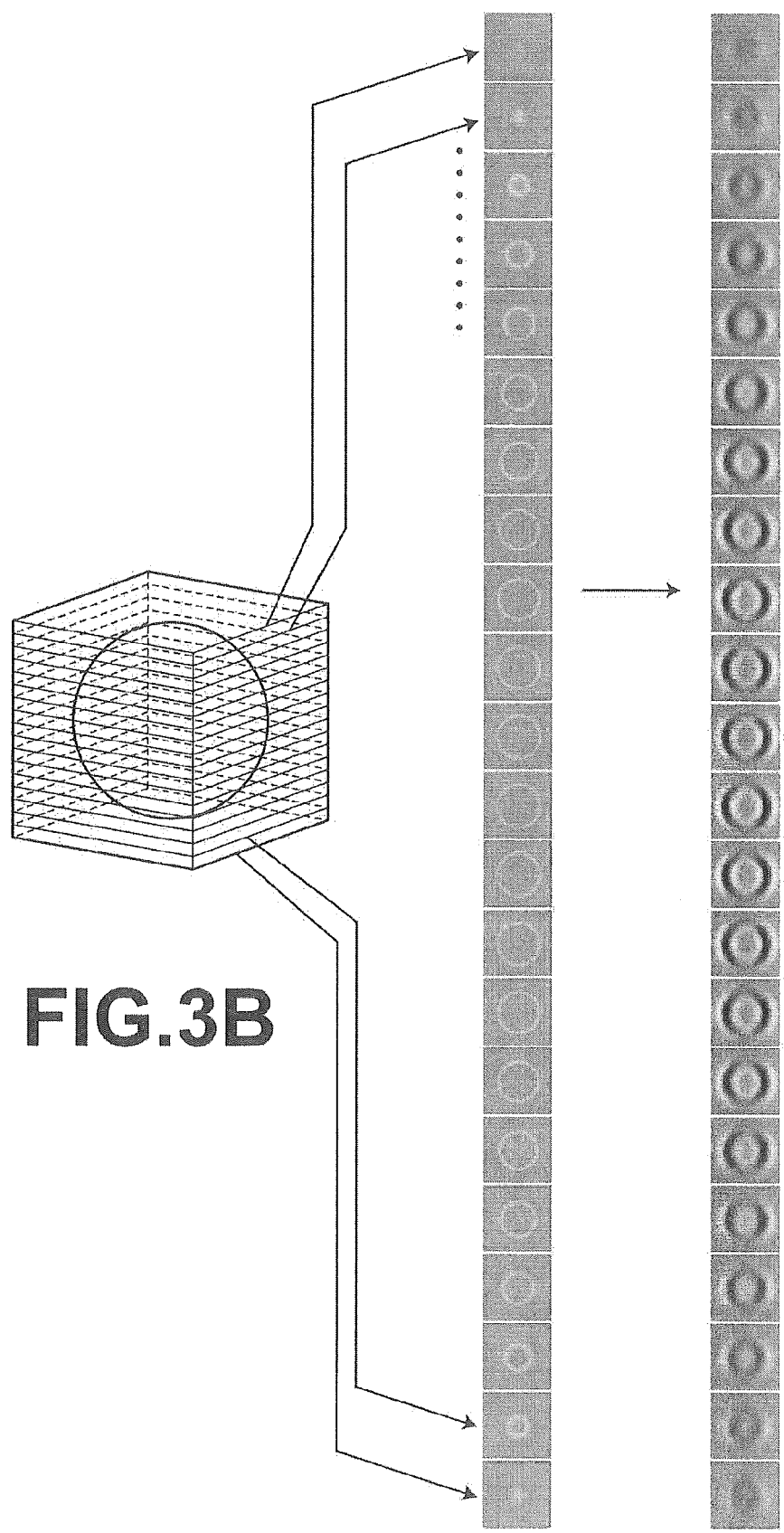
FIG. 3B is a drawing for explaining a solid sphere model function (part 2).

Hereinafter, the hollow sphere model function f(r) will be described with reference to FIGS. 3A and 3B. FIG. 3A shows a response of the hollow sphere model function f(r) in x direction by the solid line and a response of the second order partial differential of the hollow sphere model function f(r) in x direction by the broken line. The center of FIG. 3B shows the response of the hollow sphere model function f(r) by x-y plan views cut at equal intervals in the z-axis direction. The right-hand side of FIG. 3B shows the response of the second order partial differential in x direction of the hollow sphere model function f(r) by x-y plan views cut at equal intervals in the z axis direction. Both in the center and the right-hand side of FIG. 3B, the plan views representing the respective responses are arranged in descending order of z coordinate values from the top in the vertical direction. In the x-y plan views, the higher (whiter) the brightness, the greater the filter coefficient in positive value and the smaller (darker) the brightness, the greater the filter coefficient in negative value (the greater the filter coefficient in absolute value).

If the filtering is performed on a hollow structure by applying the hollow sphere mode function as shown in FIG. 3A, if a contour portion of the hollow structure correspond to a sphere wall (portion where r=−R, R)) of the hollow sphere model, the response obtained from Formula (2) is favorably large, thereby allowing very accurate discrimination. Therefore, it is preferable that the resolution of the three-dimensional multiple resolution images Msi be set such that the radius R corresponds to the line segment traversing the detection target structure, for example, the diameter of a tubular structure such as a bronchus.

The evaluation unit 34 applies eigenvalue decomposition to the Hessian matrix calculated by the filtering unit 32 and calculates three eigenvalues $\lambda_1$, $\lambda_2$, and $\lambda_3$ ($|\lambda_1| \le |\lambda_2| \le |\lambda_3|$). Then, as shown in Formulae (9) and (10), the evaluation value L0 (lineness) of line-like structureness and the evaluation value P0 (planeness) of plane-like structureness at each pixel of the three-dimensional multiple resolution image Msi are calculated. As described above, the evaluation unit 34 may discriminate a point-like structure, a line-like structure, and a plane-like structure based on the eigenvectors $e_1$, $e_2$, $e_3$ corresponding respectively to $\lambda_1$, $\lambda_2$, $\lambda_3$, but it is not necessarily to evaluate all of the point-like structure, line-like structure, and plane-like structure, and may perform discrimination for only some of the point-like structure, line-like structure, and plane-like structure according to the requirements of the specifications. As the present embodiment intends to extract a line-like structure and a plane-like structure from a medical image, evaluation values are calculated only for the line-like structure and the plane-like structure.

$$L0(\text{Lineness}) = \left(1 - \exp\left(-\frac{R_A^2}{2a^2}\right)\right)\exp\left(-\frac{R_B^2}{2b^2}\right)\left(1 - \exp\left(-\frac{S_{2nd}^2}{2c^2}\right)\right) \quad (9)$$

$$P0(\text{Planeness}) = \exp\left(-\frac{R_A^2}{2e^2}\right)\exp\left(-\frac{R_C^2}{2f^2}\right)\left(1 - \exp\left(-\frac{S_{2nd}^2}{2g^2}\right)\right) \quad (10)$$

Note that a to h in Formulae (9) and (10) are constants. Further, $R_A$, $R_B$, $R_C$ are calculated by Formulae (11) to (13) given below. Still further, $S_{2nd}$ is the power of the second order partial differential value and calculated by Formula (14) given below.

$$R_A = \frac{|\lambda_2|}{|\lambda_3|} \quad (11)$$

$$R_B = \frac{|\lambda_1|}{\sqrt{\lambda_2 \lambda_3}} \quad (12)$$

$$R_C = \frac{\sqrt{\lambda_1 \lambda_2}}{|\lambda_3|} \quad (13)$$

$$S_{2nd} = \sqrt{\lambda_1^2 + \lambda_2^2 + \lambda_3^2} \quad (14)$$

In the present embodiment, the evaluation value L0 of line-like structureness and the evaluation value P0 of plane-like structureness are calculated in the three-dimensional multiple resolution images Msi having different resolutions. The calculated evaluation values L0, P0 serve as evaluation values at a corresponding pixel position of the original three-dimensional image M0, but the evaluation values are calculated at corresponding pixel positions of all of the three-dimensional multiple resolution images Msi.

The segmentation unit 40 segments a bronchus region and the region other than the bronchus region of the three-dimensional image M0 based on the evaluation value L0 of line-like structureness and the evaluation value P0 of plane-like structureness calculated by the discrimination unit 30. More specifically, the bronchus region is set as a target region while the region other than the bronchus region is set as a background region, then a discrimination region of a predetermined pixel size is set at all pixel positions within the three-dimensional image M0, and the discrimination regions are divided into target regions and background regions using a graph cut segmentation method. The graph cut segmentation method is described in Y. Y. Boykov and M. P. Jolly, "Interactive Graph Cuts for Optimal Boundary & Region Segmentation of Objects in N-D Images", Proceedings of International Conference on Computer Vision, Vol. I, pp. 105-112, 2001. In the present embodiment, the segmentation unit 40 segments the bronchus region and the region other than the bronchus region of the three-dimensional image M0 by the method which is the same as that described in Japanese Unexamined Patent Publication No. 2011-206531, which is a past application by the present inventor, based on the evaluation value L0 of line-like structureness and evaluation value P0 of plane-like structureness calculated by the discrimination unit 30.

The display unit 50 is a monitor, a CRT screen, or the like that displays a two-dimensional image, a three-dimensional image, and the like. In the present embodiment, a line-like structure or a plane-like structure may be overviewed and the continuity thereof may be visualized by performing a volume rendering display of the line-like structure segmented as the target region on the display unit 50.

The input unit 60 includes a keyboard, a mouse, and the like.

Next, processing performed in the present embodiment will be described. FIG. 6 is a flowchart of processing performed in the present embodiment. First, the image obtaining unit 10 generates a three-dimensional image M0 from two dimensional images captured by the X-ray CT system 2 (step ST1). Then, the detection region setting unit 20 makes the three-dimensional image M0 isotropic and generates a plurality of three-dimensional multiple resolution images Msi having different resolutions by performing a multiple resolution transformation on the three-dimensional image M0 (step ST2).

Next, the filtering unit 32 of the discrimination unit 30 performs filtering on each of the three-dimensional multiple resolution images Msi using a hollow sphere model function and a Gaussian kernel function and calculates a Hessian matrix at each pixel position (step ST3). Then, the evaluation unit 34 calculates an evaluation value L0 of line-like structureness and an evaluation value P0 of plane-like structureness based on each calculated Hessian matrix (step ST4).

Next, the segmentation unit 40 divides the three-dimensional image M0 into a target region (bronchus region) and a background region using the aforementioned graph cut segmentation method (step ST5). Then, the display unit 50 performs a volume rendering display of the divided target region and the background region (step ST6) and the processing is completed.

As described above, according to the present embodiment, the filtering unit 32 that calculates an evaluation matrix by filtering on each pixel position of an image representing a hollow structure using second order partial differential matrix of a hollow sphere model function, and the evaluation unit 34 that calculates an evaluation value of at least one or more of point-like structureness, line-like structureness, and plane-like structureness on each pixel position based on the calculated evaluation matrix. This allows image filtering by a function representing a hollow sphere appropriately representing structural characteristics of a discrimination target to be performed. Consequently, the evaluation accuracy of an evaluated structure or structures of point-like structure, line-like structure, and plane-like structure of a hollow structure included in an image may be improved based on evaluation values calculated from an evaluation matrix obtained as a result of the appropriate filtering.

Further, in the first embodiment described above, an evaluation matrix is calculated with respect to functions representing the hollow sphere with radius R in a plurality of sizes, by performing filtering using second order partial differential matrix of a function representing each hollow sphere, and evaluation values of line-like structureness and plane-like structureness are calculated at each pixel position based on the plurality of evaluation matrices. Consequently, a structure having a size corresponding to each kernel size may be evaluated appropriately. Further, if the target region is segmented, as in the first embodiment based on the evaluation value, hollow structures of a plurality of sizes may be segmented as target regions.

As the method for performing Hessian analysis on structures of different sizes, a method that performs Hessian analysis on the images of a plurality of different resolutions by applying a constant kernel size "σ" and a constant radius R of hollow sphere model function may be used, as in the present embodiment, or a method that performs Hessian analysis on an image of a constant resolution by applying different constant kernel sizes "σ" and different radii R of hollow sphere model functions may be used, and the same effects may be obtained from them. For example, it is conceivable that the length of a line segment traversing a detection target structure, such as the long axis and the short axis of the hollow structure, are obtained in advance from experimentally obtained data and the resolution of the three-dimensional multiple resolution image Msi or the kernel size "σ" and the radius R are set such that the length of a line segment traversing a detection target structure corresponds to the size of the radius R.

In order to restrict the calculation load and speed up the calculation, it is preferable that the filtering is performed in Fourier space as in the present embodiment, but the filtering may be performed by convoluting the second order partial differential of the hollow sphere model function f(r) and Gaussian kernel with a target image in real space.

In the first embodiment described above, both the evaluation value L0 of line-like structureness and the evaluation value P0 of plane-like structureness are calculated, but either one of the evaluation value L0 of line-like structureness and the evaluation value P0 of plane-like structureness may be calculated.

Further, in the first embodiment described above, the evaluation value L0 of line-like structureness and the evaluation value P0 of plane-like structureness are calculated using the eigenvalues obtained by applying eigenvalue decomposition to the Hessian matrix. But, the evaluation value of line-like structureness and the evaluation value of plane-like structureness may be calculated by directly using the elements of the Hessian matrix.

As a second embodiment of the present invention, an image processing apparatus for direction discrimination will be described hereinafter. FIG. 7 is a functional block diagram of the image processing apparatus for direction discrimination.

The image processing apparatus in the second embodiment does not include the segmentation unit 40, the evaluation unit 34, and the display unit 50 in the first embodiment, but includes a direction discrimination unit 35 instead. Processing other than direction discrimination processing performed by the direction discrimination unit 35, that is, the image obtaining processing performed by the image obtaining unit 10, the detection region setting processing performed by the detection region setting unit 20, and the filtering processing performed by the filtering unit 32 are identical to those of the first embodiment and the function of each functional block is also common. Hereinafter, a description will be made focusing on the difference from the first embodiment and the description for the identical points will be omitted here.

The direction discrimination unit 35 calculates eigenvalues and eigenvectors $e_1$, $e_2$, $e_3$ by performing eigenvalue analysis on the evaluation matrix calculated by the filtering unit 32, and discriminates a principal axis direction of a line-like structure or a normal direction of a plane-like structure based on the directions of the calculated eigenvectors. More specifically, the direction discrimination unit 35 obtains $\lambda_1$, $\lambda_2$, and eigenvectors $e_1$, $e_2$, $e_3$ of the Hessian matrix obtained by the filtering unit 32 and discriminates the direction pointed by the eigenvector $e_1$ corresponding to the eigenvalue $\lambda_1$ as the axis direction of the line-like structure, if the relationship indicated in Formula (6) is satisfied and, if the relationship indicated in Formula (7) is satisfied, discriminates the direction pointed by the eigenvector $e_2$ corresponding to the eigenvalue $\lambda_2$ as the normal direction of the plate-like structure.

FIG. 8 is a flowchart of processing performed in the present embodiment. First, the image obtaining unit 10 generates a three-dimensional image M0 from two dimensional images captured by the X-ray CT system 2 (step ST11). Then, the detection region setting unit 20 makes the three-dimensional image M0 isotropic and generates a plurality of three-dimensional multiple resolution images Msi having different resolutions by performing a multiple resolution transformation on the three-dimensional image M0 (step ST12).

Next, the filtering unit 32 of the discrimination unit 30 performs filtering on each three-dimensional multiple resolution image Msi using a hollow sphere model function and a Gaussian kernel function and calculates a Hessian matrix at each pixel position (step ST13). Then, the direction discrimination unit 35 obtains local eigenvalues and eigenvectors of each pixel based on the Hessian analysis result and calculates the axis direction of the line-like structure or the normal direction of the plane-like structure based on Formulae (6) and (7) as described above (step ST14), and the processing is completed.

As described above, also in the second embodiment, filtering of an image may be performed by a function representing a hollow sphere that appropriately represents structural characteristics of a discrimination target, as in the first embodiment. Consequently the accuracy of eigenvalues and eigenvector values calculated from the evaluation matrix may be improved. Therefore, an axis direction of a line-like structure or a normal direction of a plane-like structure may be discriminated appropriately at each position of a hollow structure based on the eigenvalues and eigenvectors. The axis direction of a line-like structure and the normal direction of a plane-like structure obtained by the image processing apparatus of the second embodiment described above may be used, for example, as the axis direction when generating a CPR (Curved Planar Reformation/Reconstruction) image of a tubular structure, such as a bronchus, a large intestine, or the like, reconstructed from a three-dimensional image by the CPR method, and are favorably used in various types of known processing that requires the axis direction of a line-like structure and the normal direction of a plane-like structure. The axis direction of a line-like structure and the normal direction of a plane-like structure obtained by the present invention may be used for various types of known CPR image generation methods, including, for example, A. Kanitsar et al., "CPR—Curved Planar Reformation", IEEE Visualization, 2002.

Further, also in the second embodiment, an evaluation matrix is calculated with respect to functions representing the hollow sphere with radius R in a plurality of sizes by performing filtering using second order partial differential matrix of a function representing each hollow sphere, and eigenvalues and eigenvectors are calculated at each pixel position based on the plurality of evaluation matrices. Consequently, with respect to a structure having a size corresponding to each kernel size, the axis direction of a line-like structure or the normal direction of a plane-like structure may be discriminated appropriately.

Note that the direction discrimination unit 35 may discriminate only either one of the axis direction of a line-like structure according to Formula (6) and the normal direction of a plane-like structure according to Formula (7) based on the eigenvalues and the eigenvectors of the Hessian matrix.

As the image is a medical image and the tubular structure is a bronchus in each embodiment described above, the function representing the hollow sphere used for the filtering and the hollow structure included in the image well correspond to each other in structural characteristics, so that evaluation values of at least one or more of point-like structureness, line-like structureness, and plane-like structureness may be calculated very accurately in the first embodiment. Further, in the second embodiment, the axis direction of a line-like structure or the normal direction of a plane-like structure may be discriminated very accurately.

In each embodiment described above, discrimination of bronchus is described as an example of line-like structure, but the discrimination method may be applied to the other structures as long as they are hollow structures. Further, the discrimination method may be applied to an image which includes both a hollow structure and a solid structure, such as a blood vessel or the like, and an image which includes both a hollow structure and a plane structure, such as bone, skin, interlobar membrane, and the like.

In each embodiment described above, each evaluation processing or direction discrimination processing is performed with a line-like structure and a plane-like structure included in a three-dimensional image M0 as targets, but each evaluation processing or direction discrimination processing may be performed with a line-like structure and a plane-like structure included in a two-dimensional image as targets.

Further, in each embodiment described above, a line-like structure and a plane-like structure are segmented using a graph cut segmentation method but, of course, other segmentation methods, such as the watershed algorithm and the like, may also be used. The watershed algorithm is a method of segmenting an image like, when water is filled in a terrain in which pixel value information of the image is regarded as height, a boundary is formed between water accumulated in different depressions. Therefore, the line-like structure and the plane-like structure may be segmented by performing appropriate smoothing processing on the evaluation values L0 and P0 of the three-dimensional image M0 and implementing the watershed algorithm.

It should be appreciated that each embodiment described above is for illustration purposes only, and any of the above descriptions should not be used to interpret the technical scope of the present invention in a limited way.

In addition, various modifications made to the system configurations, hardware configurations, processing flows, module organizations, user interfaces, specific processing contents, and the like of the embodiments described above without departing from the spirits of the present invention are included in the technical scope of the present invention.

What is claimed is:

1. An image processing apparatus, comprising:
   a filter that is configured to calculate a Hessian matrix on each pixel position of an image representing a hollow structure by convoluting a filter kernel representing a second order partial differential of a function representing a hollow sphere; and
   an evaluation unit that is configured to calculate an evaluation value of at least one or more of hollow-point-like structureness, hollow-line-like structureness, and hollow-plane-like structureness at the pixel position based on the calculated Hessian matrix.

2. An image processing apparatus, comprising:
   a filter that is configured to calculate an evaluation Hessian matrix by performing filtering on each pixel position of an image representing a hollow structure using by convoluting a filter kernel representing a second order partial differential of a function representing a hollow sphere; and
   a direction discrimination unit that is configured to calculate eigenvalues and eigenvectors by performing eigenvalue analysis on the calculated Hessian matrix and discriminates, based on directions of the calculated eigenvectors, a principal axis direction of a hollow-line-like structure or a normal direction of a hollow-plane-like structure.

3. The image processing apparatus as claimed in claim 1, wherein the function representing the hollow sphere is expressed by Formula (3) given below:

$$\left.\begin{array}{l} f(r) = \delta(r - R) \\ r = \sqrt{x^2 + y^2 + z^2} \end{array}\right\} \quad (3)$$

where, x, y, z are three-dimensional coordinates in real space and R is the radius of the hollow sphere.

4. The image processing apparatus as claimed in claim 1, wherein the filter calculates respectively, with respect to functions representing the hollow sphere in a plurality of sizes, Hessian matrixes by using filters representing a second order partial differential of the function representing each hollow sphere.

5. The image processing apparatus as claimed in claim 1, wherein the filter calculates the Hessian matrix in Fourier space.

6. The image processing apparatus as claimed in claim 1, wherein the image is a medical image, and the hollow structure is a bronchus.

7. An image processing method performed by a computer having a processor and a memory, comprising:
   calculating a Hessian matrix by performing filtering on each pixel position of an image representing a hollow structure by convoluting a filter kernel representing a second order partial differential of a function representing a hollow sphere; and
   calculating an evaluation value of at least one or more of hollow-point-like structureness, hollow-line-like structureness, and hollow-plane-like structureness at the pixel position based on the calculated Hessian matrix.

8. A non-transitory computer readable recording medium on which is recorded an image processing program that causes a computer to function as, comprising:
   a filter that is configured to calculate a Hessian matrix on each pixel position of an image representing a hollow structure by convoluting a filter kernel representing a second order partial differential of a function representing a hollow sphere; and
   an evaluation unit that is configured to calculate an evaluation value of at least one or more of hollow-point-like structureness, hollow-line-like structureness, and hollow-plane-like structureness at the pixel position based on the calculated Hessian matrix.

9. The image processing apparatus as claimed in claim 2, wherein the function representing the hollow sphere is expressed by Formula (3) given below:

$$\left.\begin{array}{l} f(r) = \delta(r - R) \\ r = \sqrt{x^2 + y^2 + z^2} \end{array}\right\} \quad (3)$$

where, x, y, z are three-dimensional coordinates in real space and R is the radius of the hollow sphere.

10. The image processing apparatus as claimed in claim 2, wherein the filter calculates respectively, with respect to functions representing the hollow sphere in a plurality of sizes, Hessian matrixes by using filters representing a second order partial differential of the function representing each hollow sphere.

11. The image processing apparatus as claimed in claim 2, wherein the filter calculates the Hessian matrix in Fourier space.

12. The image processing apparatus as claimed in claim 2, wherein the image is a medical image, and the hollow structure is a bronchus.

13. The image processing apparatus as claimed in claim 3, wherein the evaluation unit calculates the evaluation value of at least one or more of hollow-point-like structureness, hollow-line-like structureness, and hollow-plane-like structureness, where the hollow size corresponds to the radius R of the hollow sphere.

* * * * *